(12) United States Patent
Nagai et al.

(10) Patent No.: US 9,638,610 B2
(45) Date of Patent: May 2, 2017

(54) SAMPLE PROCESSING APPARATUS

(71) Applicant: SYSMEX CORPORATION, Kobe-shi, Hyogo (JP)

(72) Inventors: Takaaki Nagai, Kobe (JP); Daigo Fukuma, Kobe (JP); Mitsuo Yamasaki, Kobe (JP); Noriyuki Nakanishi, Kobe (JP); Syunsuke Yao, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 256 days.

(21) Appl. No.: 14/578,564

(22) Filed: Dec. 22, 2014

(65) Prior Publication Data

US 2015/0185119 A1    Jul. 2, 2015

(30) Foreign Application Priority Data

Dec. 27, 2013   (JP) ................ 2013-272556

(51) Int. Cl.

| | |
|---|---|
| *G01N 1/28* | (2006.01) |
| *B01L 3/00* | (2006.01) |
| *B01L 9/06* | (2006.01) |
| *G01N 35/02* | (2006.01) |
| *G01N 35/00* | (2006.01) |
| *G01N 35/04* | (2006.01) |

(52) U.S. Cl.
CPC ............ *G01N 1/28* (2013.01); *B01L 3/5082* (2013.01); *B01L 3/54* (2013.01); *B01L 9/06* (2013.01); *G01N 35/026* (2013.01); *B01L 2200/023* (2013.01); *B01L 2200/143* (2013.01); *B01L 2300/021* (2013.01); *B01L 2300/044* (2013.01); *B01L 2300/0672* (2013.01); *G01N 2035/00752* (2013.01); *G01N 2035/00772* (2013.01); *G01N 2035/00801* (2013.01); *G01N 2035/041* (2013.01); *G01N 2035/0493* (2013.01)

(58) Field of Classification Search
CPC ................ G01N 1/28; B01L 3/00; B01L 9/06
USPC .......... 422/63, 64, 65, 66, 67, 68.1, 81, 549, 422/552, 560, 561, 562; 436/43
See application file for complete search history.

(56) References Cited

U.S. PATENT DOCUMENTS

| | | | |
|---|---|---|---|
| 5,235,193 A | 8/1993 | Hürlimann | |
| 5,314,825 A | * 5/1994 | Weyrauch et al. ............ | 436/43 |
| 5,721,384 A | 2/1998 | Tanihata | |
| 2006/0245865 A1 | * 11/2006 | Babson ................... | 414/331.01 |

(Continued)

FOREIGN PATENT DOCUMENTS

| | | |
|---|---|---|
| EP | 0485825 A1 | 5/1992 |
| GB | 1429052 A | 3/1976 |

(Continued)

*Primary Examiner* — Brian J Sines
(74) *Attorney, Agent, or Firm* — Mots Law, PLLC

(57) ABSTRACT

Disclosed is a sample processing apparatus that comprises a rack with positions to hold sample tubes, the rack including a rack identification suited to a kind of sample tube, a rack set unit that accepts the rack in a detachable manner, a tube transfer unit with mechanical movement to grab and take out each sample tube from a rack held in the rack set unit, a rack detector comprising a sensor to detect the rack identification of the rack held in the rack set unit, and a controller that controls movement of the tube transfer unit based on a detection result of the rack detector.

20 Claims, 14 Drawing Sheets

(56) References Cited

U.S. PATENT DOCUMENTS

| | | | |
|---|---|---|---|
| 2009/0130745 A1* | 5/2009 | Williams et al. | 435/287.2 |
| 2011/0071039 A1* | 3/2011 | Kumar et al. | 506/9 |
| 2011/0158850 A1 | 6/2011 | Pedrazzini | |

FOREIGN PATENT DOCUMENTS

| | | | |
|---|---|---|---|
| JP | H05-281236 A | 10/1993 |
| JP | 2000-346851 A | 12/2000 |
| JP | 2005-091277 A | 4/2005 |
| JP | 2007-093297 A | 4/2007 |
| JP | 2007-139462 A | 6/2007 |
| JP | 2008-046033 A | 2/2008 |
| JP | 2010-181197 A | 8/2010 |

* cited by examiner

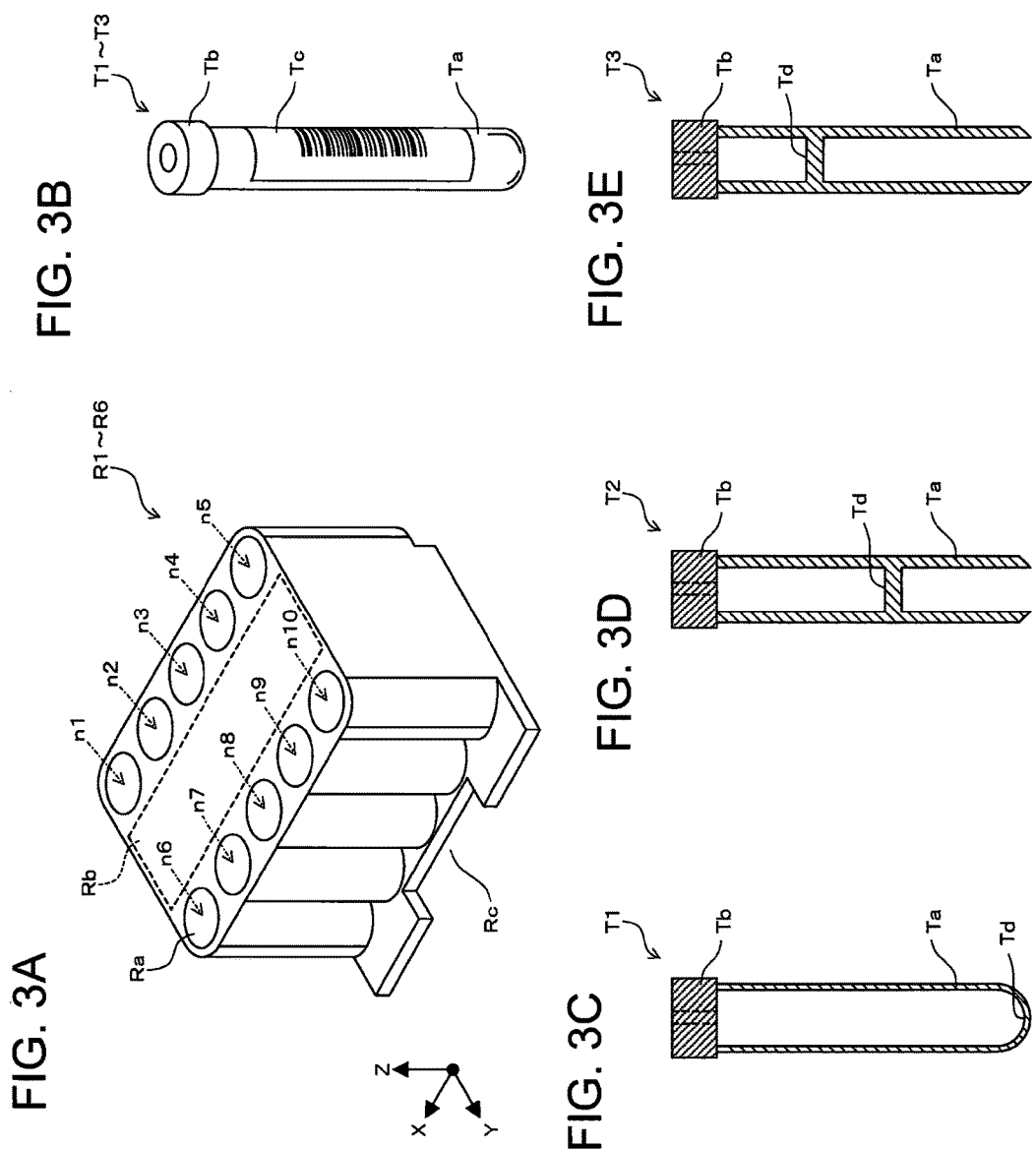

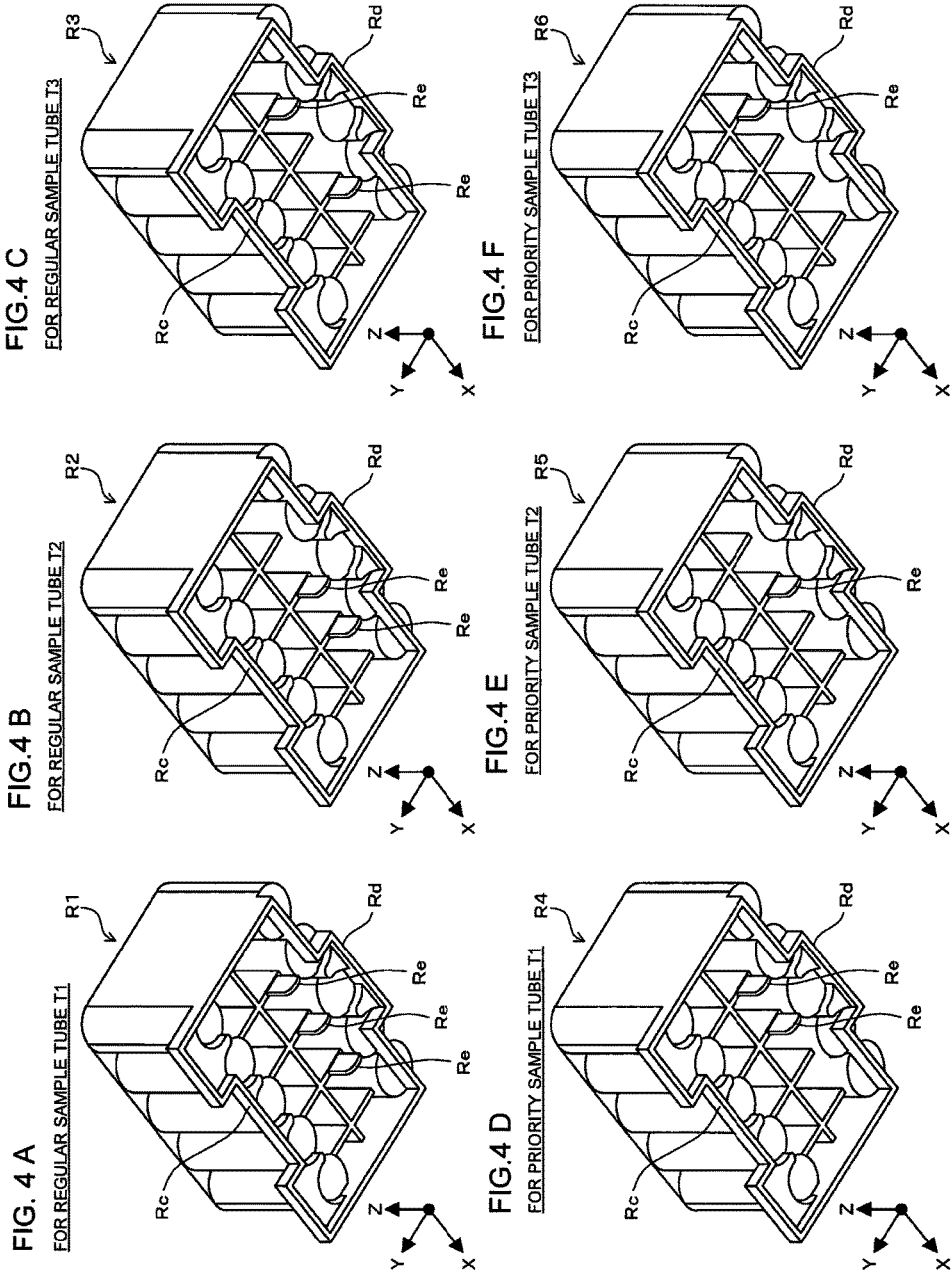

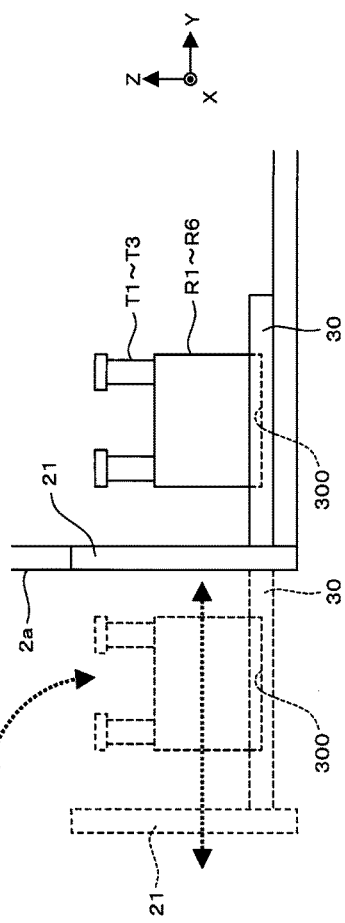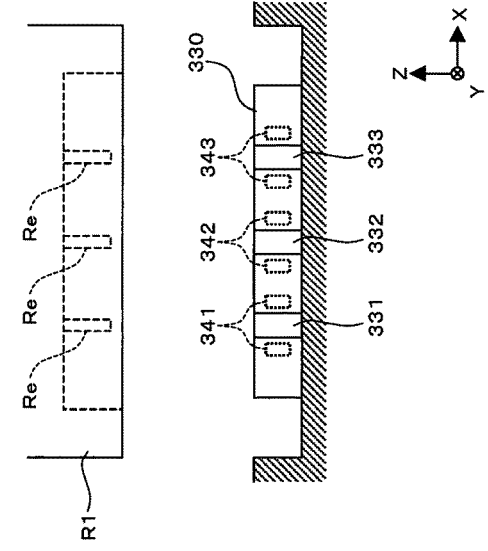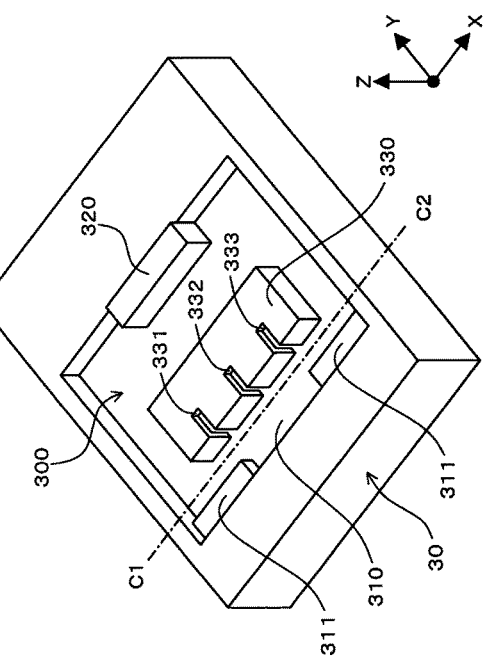

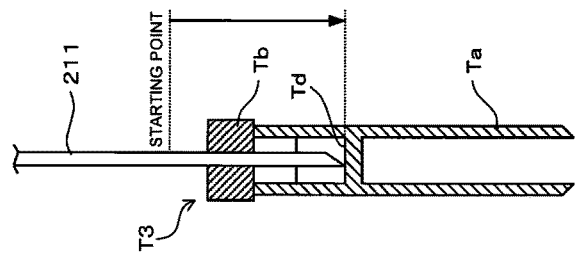
FIG. 7D
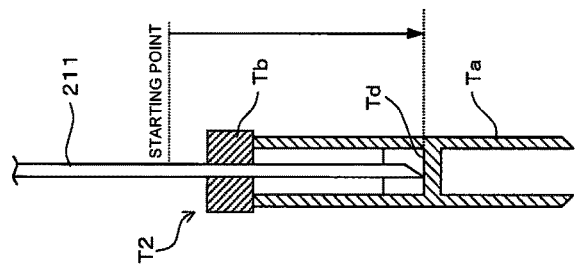
FIG. 7C
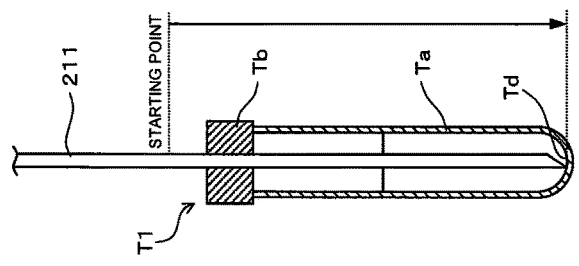
FIG. 7B
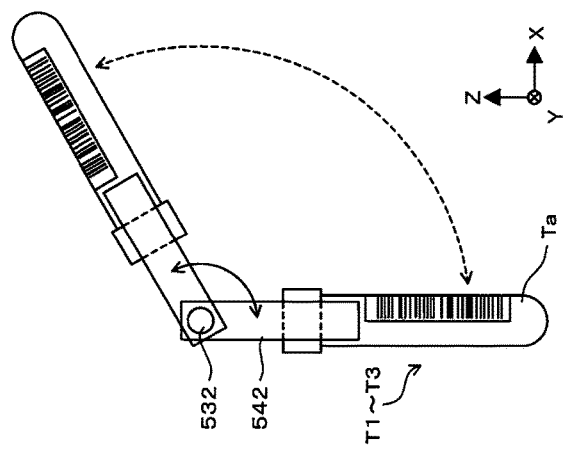
FIG. 7A
FIG. 7E
SETTING TABLE
| KIND OF SAMPLE TUBE | NUMBER OF TURNOVERS | NUMBER OF PULSES |
|---|---|---|
| SAMPLE TUBE T1 | fn1 | pn1 |
| SAMPLE TUBE T2 | fn1 | pn2 |
| SAMPLE TUBE T3 | fn2 | pn3 |

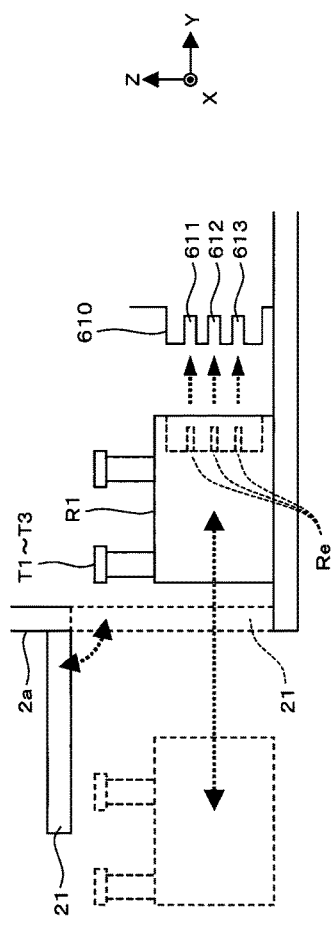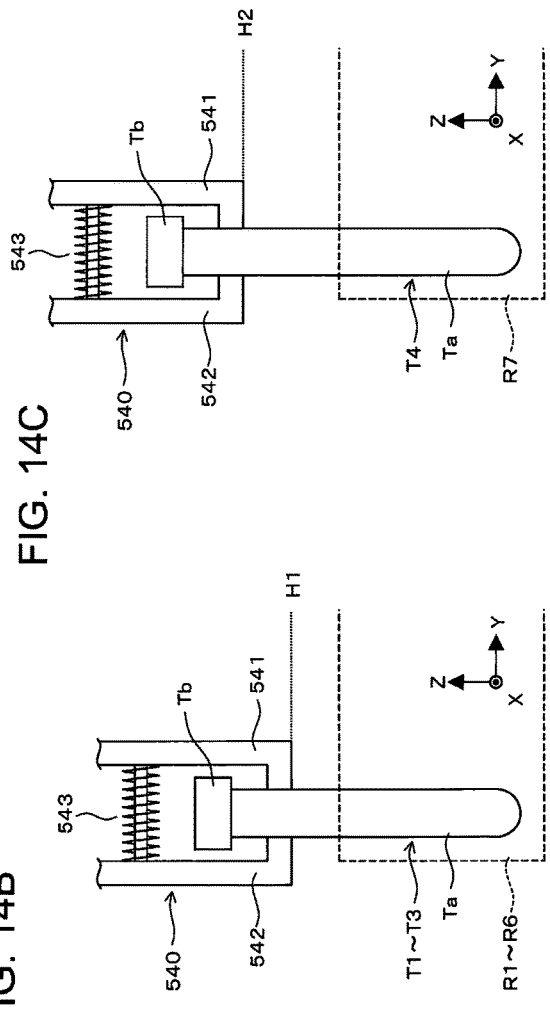

SAMPLE PROCESSING APPARATUS

CROSS REFERENCE TO RELATED APPLICATIONS

This application claims priority from prior Japanese Patent Applications No. 2013-272556, filed on Dec. 27, 2013, entitled "SAMPLE PROCESSING APPARATUS AND RACK", the entire contents of which are incorporated herein by reference.

FIELD OF THE INVENTION

The invention relates to a sample processing apparatus and a rack, which is used for the sample processing apparatus.

BACKGROUND

There is known a sample analyzer in which a sample tube supply unit transfers one of multiple sample tubes held in a rack to a sample rack set unit and sets the sample tube in the sample rack set unit, a sample in the set sample tube is aspirated, and a measurement unit measures the aspirated sample (see Japanese Patent Application Publication No. 2007-139462).

Various kinds of sample tubes are used in a sample processing apparatus. Every time a sample tube is changed, an operator has to correctly change conditions for transferring the sample tube according to the type of sample tube.

For example, in some cases, the sample processing apparatus uses various sample tubes having different lengths. In such a case, an operator has to change conditions for transferring sample tubes so that a grip position of the sample tube can be changed according to the length of the sample tube. There is also another situation where the sample processing apparatus uses a sample tube holding a priority sample, for example. In this case, an operator has to change the conditions for transferring the sample tube so that the sample tube holding the priority sample can be transferred preferentially to the other sample tubes.

SUMMARY OF THE INVENTION

The scope of the invention is defined by the appended claims, and not by any statements within this summary.

An embodiment is a sample processing apparatus. The sample processing apparatus includes a rack configured to hold sample tubes and includes a rack identification portion suited to sample tube type, a rack set unit where the rack is set in a detachably-attached manner, a tube transfer unit configured to take out and transfer each of the sample tubes from the rack set in the rack set unit, a rack detector configured to detect the rack identification portion in the rack set in the rack set unit, and a controller configured to control an operation of the tube transfer unit based on a detection result of the rack detector.

BRIEF DESCRIPTION OF DRAWINGS

FIG. 3A is a perspective view illustrating a case where a rack according to the embodiment is seen from above;

FIG. 3B is a diagram illustrating an outside appearance of a sample tube according to the embodiment;

FIGS. 3C and 3E are cross-sectional diagrams of the sample tube according to the embodiment;

FIGS. 4A to 4F are perspective diagrams, each illustrating a case where the rack according to the embodiment is seen from below;

FIG. 5A is a schematic diagram illustrating forward and backward movements of a drawer according to the embodiment;

FIG. 5B is a diagram illustrating a configuration of the drawer according to the embodiment;

FIG. 5C is a diagram illustrating a case where a cut-apart rack set unit is seen from the front thereof;

FIG. 7A is a diagram illustrating stirring processing by the stirrer mechanism according to the embodiment;

FIGS. 7B to 7D are diagrams, each illustrating aspiration processing by an aspiration unit according to the embodiment;

FIG. 7E is a conceptual diagram illustrating a configuration of a setting table stored in a hard disk according to the embodiment;

FIG. 14A is a schematic diagram illustrating that the rack according to the modified embodiment is directly set in a case;

FIG. 14B is a diagram illustrating a grip position at which the sample tube according to the embodiment is held; and FIG. 14C is a diagram illustrating a grip position at which the sample tube according to the modified embodiment is held.

DETAILED DESCRIPTION

An embodiment is a sample analyzer configured to examine and analyze blood. Hereinafter, a sample analyzer according to the embodiment is described by referring to drawings.

Figure 1:
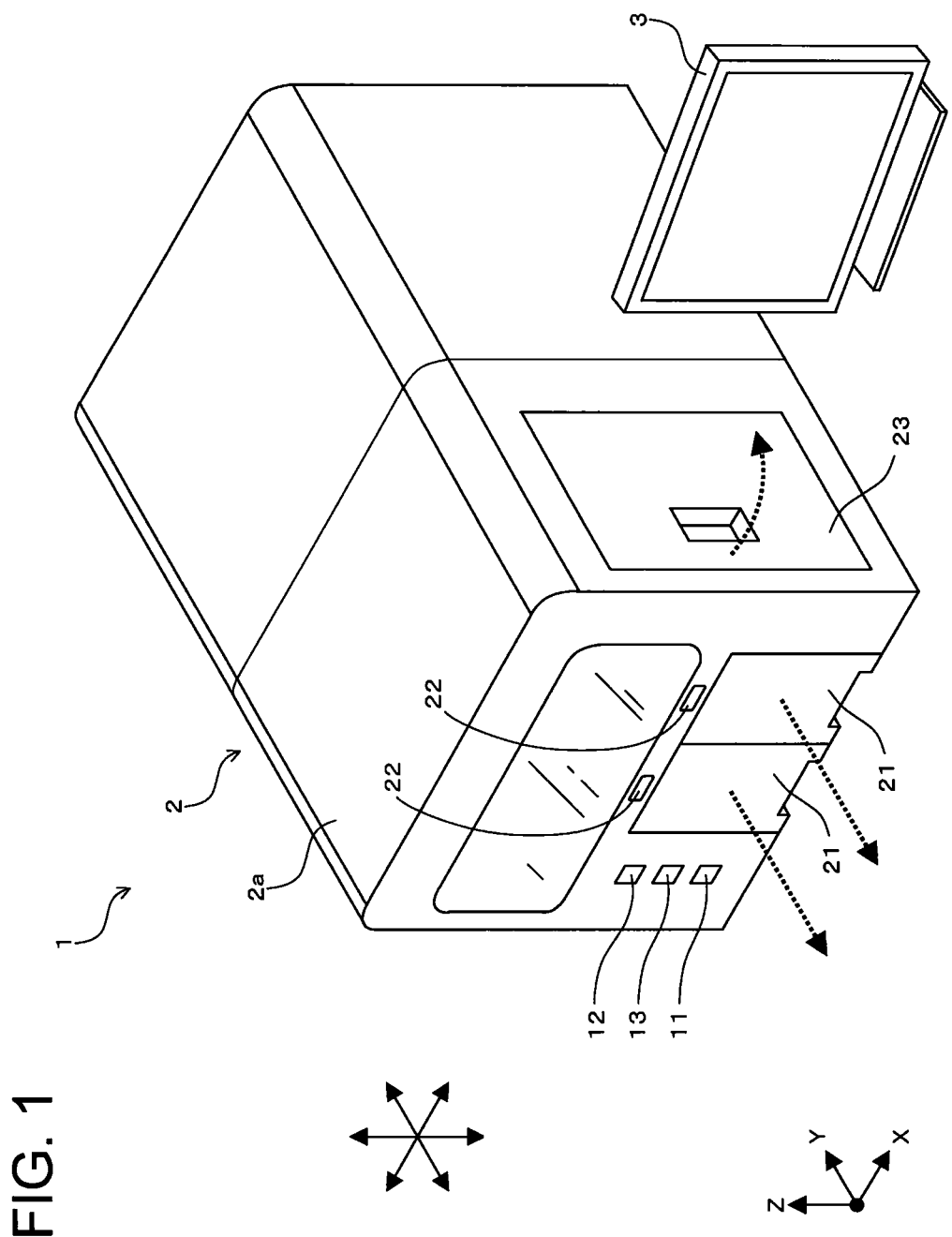
FIG. 1 is a schematic diagram illustrating an outside appearance of a sample analyzer according to an embodiment.

FIG. 1 is a diagram illustrating an outside appearance of sample analyzer 1 according to embodiments.

Sample analyzer 1 includes main body 2 and display input unit 3, which is a touch panel display. Main body 2 is covered with case 2a and is provided with power button 11 configured to operate a power source of sample analyzer 1, start button 12, stop button 13, two panels 21, and two lamps 22 on the front side of case 2a. Drawers 30 (see, FIG. 2) are provided respectively on the back sides of two panels 21. Two lamps 22 indicate states of corresponding drawers 30. Openable/closable door 23 is provided on the front side of the right side surface of case 2a.

When processing multiple samples (hereinafter, referred to as "sampler processing"), an operator pulls drawer 30 by pulling panel 21, sets a rack holding sample tubes into drawer 30, and then pushes start button 12. In addition, when preferentially processing one sample (hereinafter referred to as "manual processing"), the operator opens door 23 and sets sample tubes into the tube set unit 71 (see, FIG. 2) inside case 2a and pushes start button 83 (see, FIG. 2) inside case 2a.

Figure 2:
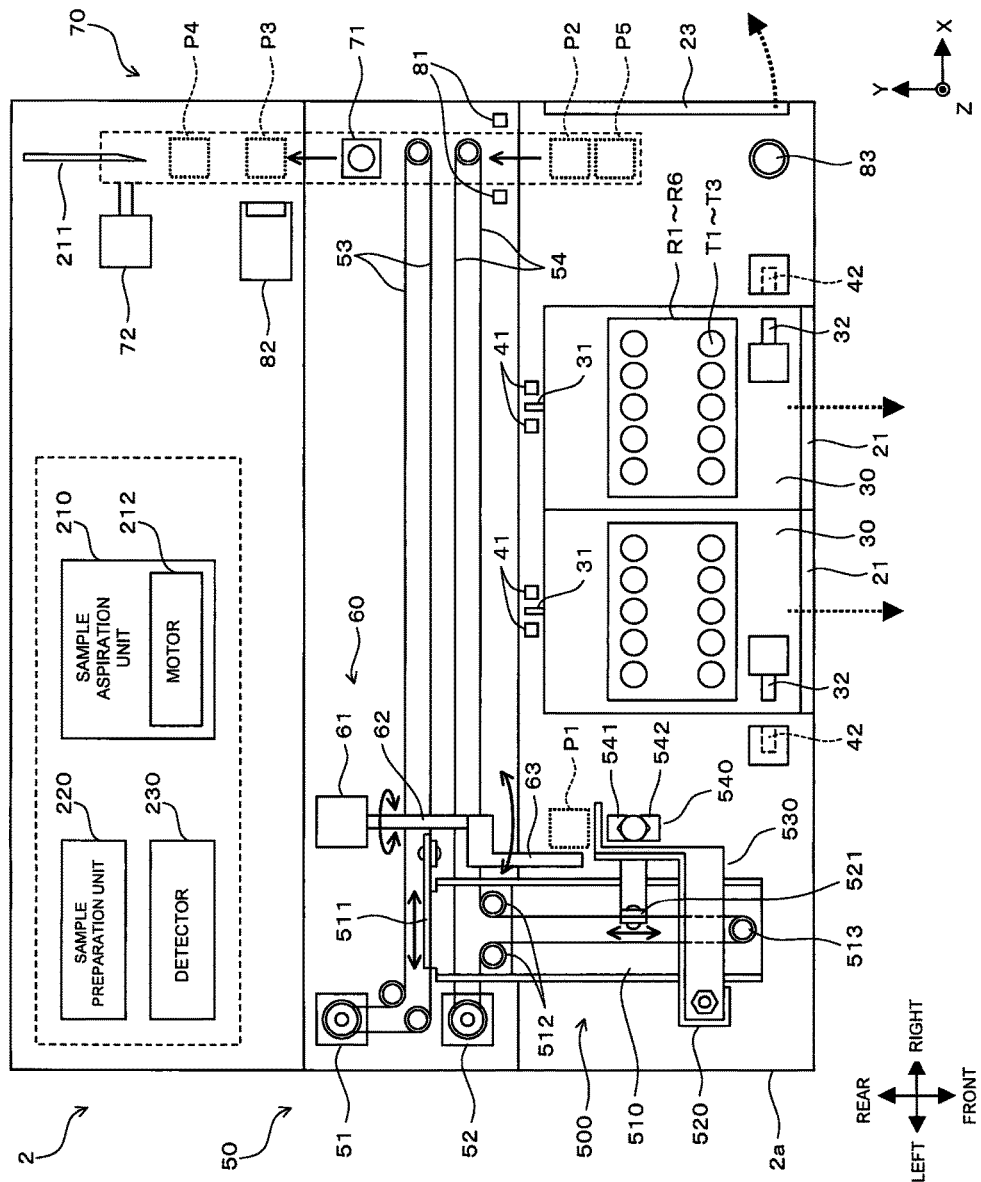
FIG. 2 is a schematic diagram illustrating a case where an inside of a case according to the embodiment is seen from above.

FIG. 2 is a schematic diagram illustrating an embodiment where the inside of case 2a is seen from above.

Main body 2 includes two drawers 30 configured to set racks R1 to R6 (see, FIG. 3A), transmission sensors 41 configured to respectively detect two drawers 30 being set in case 2a in a closed state, holes 42 configured to respectively fix two drawers 30, tube transfer unit 50 configured to transfer sample tubes T1 to T3 (see, FIG. 3B), stirrer mechanism 60 configured to stir a sample by turning sample tubes T1 to T3 down, back-and-forth conveyance unit 70 configured to move sample tubes T1 to T3 in back and forth directions, transmission sensor 81 configured to detect whether or not a sample tube exists in back-and-forth conveyance unit 70, barcode reader 82, start button 83, sample aspiration unit 210 configured to aspirate samples in sample tubes T1 to T3, sample preparation unit 220, detector 230, and measurement samples.

Referring to FIGS. 3A to 5C, racks R1 to R6, sample tubes T1 to T3, and drawers 30 are described.

FIG. 3A is a perspective diagram illustrating a case where racks R1 to R6 are seen from above. It is to be noted that in FIG. 3A, coordinate axes illustrated in FIG. 2, which is used when racks R1 to R6 are set in drawers 30 are also illustrated.

In the embodiment, as described later, six kinds of racks R1 to R6 are used according to kinds of sample tubes. As illustrated in FIG. 3A, shapes of racks R1 to R6 are exactly same with one another when seen from above but shapes thereof which are seen from bottom are different from one another. The shapes of racks R1 to R6 are described by referring to FIGS. 4A to 4F later.

To allow 10 sample tubes T1 to T3 to be held vertically, 10 holders Ra are formed in racks R1 to R6, and 10 holders Ra are formed so that each 5 holders Ra are arrayed in a double row in front and rear sides. As illustrated in FIG. 3A, positions of 10 holders Ra are referred to as holding position n1 to n10 for convenience. Also, the top surface of racks R1 to R6 are parallel with the X-Y plane, and intermediate portion Rb is formed between the row of holding positions n1 to n5 and the row of holding positions n6 to n10. In addition, dent portion Rc, which dents inside the periphery thereof is formed on the rear side (the Y-axis positive side) of the lower end of rack R1 to R6.

FIG. 3B is a diagram illustrating an outer appearance of sample tubes T1 to T3.

Sample tubes T1 to T3 include body portion Ta, lid portion Tb, and barcode label Tc. Body portion Ta is a tubular container configured of translucent glass or synthetic resin and has an opening formed on an upper end thereof. Body portion Ta holds a sample and the opening in the upper end is tightly sealed with lid portion Tb. Lid portion Tb is configured to allow piercer 211 (see FIG. 2) to pass therethrough. Barcode label Tc includes a barcode including sample ID printed thereon. Barcode label Tc is adhered to the side surface of body portion ta.

Each of FIGS. 3C and 3E is a cross-sectional diagram of sample tubes T1 to T3. For example, sample tubes T1 to T3 are used as blood-collecting vessels.

Bottom surface Td is formed on a lower end of an inner side of body portion Ta, and the positions of bottom surfaces Td of sample tubes T1 to T3 become higher in the order of sample tubes T1 to T3. Accordingly, volumes of samples containable in sample tubes T1 to T3 become smaller in the order of sample tubes T1 to T3.

Each of FIGS. 4A to 4F is a perspective diagram illustrating a case where racks R1 to R6 are seen from bottom (Z-axis negative side).

On the lower end of racks R1 to R6, in addition to recessed portion Rc illustrated in FIG. 3A, projection portion Rd which outwardly projects from the periphery thereof is formed on the opposite side of recessed portion Rc (the Y-axis negative side of the lower end of racks R1 to R6).

Also, on the lower surface of racks R1 to R6, projection portion Re is formed. A lower end of projection portion Re is positioned higher than the lower end of racks R1 to R6. There are three portions where projection portion Re is to be formed, and projection portion Re is formed in at least one position among these positions. Specifically, projection portion Re is formed in each of the three positions in rack R1, and projection portions Re are formed in the center and a position on the X-axis positive side in rack R2, projection portions Re are formed in positions on the X-axis positive side and the X-axis negative side in rack R3. In addition, projection portions Re are formed in the center and a position on the X-axis negative side in rack R4, and projection portion Re is formed in the center in rack R5, and projection portion Re is formed in a position on the X-axis negative side.

Here, samples according to the embodiment include regular samples whose analysis is not particularly in a hurry (hereinafter, referred to as "regular sample") and samples whose analysis has to be performed preferentially to the regular samples (hereinafter, referred to as "priority sample"). Also, three kinds of above-described sample tubes T1 to T3 are used as sample tubes. Anyone of the regular samples and the priority samples is held in each of the sample tubes T1 to T3. Accordingly, in the present embodiment, sample tubes T1 to T3 hold the regular samples, and sample tubes T1 to T3 hold the priority samples. As a result, there are six kinds of sample tubes in combination.

Also, in the embodiment, a rack to be used is determined for each of the six kinds of the sample tubes. Sample tubes T1 to T3 holding regular samples are set only in racks R1 to R3, respectively, and sample tubes T1 to T3 holding priority samples are set only in racks R4 to R6, respectively. Hereinafter, racks R1 to R3 are collectively referred to as a "regular rack" and racks R4 to R6 are collectively referred to as a "priority rack." In this manner, racks R1 to R6 in which sample tubes T1 to T3 are set according to the above rules are set in drawer 30 which is pulled out forwardly by an operator.

FIG. 5A is a schematic diagram illustrating the back and forth movements of drawer 30.

Panel 21 is connected with a front end (end portion on the Y-axis negative side) of drawer 30, which is moved back and forth along the panel 21 when an operator moves panel 21 back and forth. Also, rack set unit 300 is formed in drawer 30 for installing racks R1 to R6. When drawer 30 is moved back and forth, rack set unit 300 is also moved between a loaded position in which the rack is loaded in case 2a and a drawn position in which the rack is drawn out from case 2a.

When drawer 30 is drawn out and rack set unit 300 is positioned in the drawn position, the operator may set the rack in rack set unit 300 and may also take out the rack set in rack set unit 300. Also, when rack set unit 300 is positioned in the loaded position, processing is performed with mechanisms inside case 2a on the sample tubes held in the rack set in rack set unit 300.

FIG. 5B is a diagram illustrating the configuration of drawer 30. Here, for convenience's sake, FIG. 5B omits illustration of flange portion 31 and bar member 32 (see FIG. 2), which are to be described later.

Rack set unit 300 is formed in a position near the center of drawer 30, and the bottom surface of rack set unit 300 is formed so as to be lower by one step than the upper surface of drawer 30. In the front end and rear end of rack set unit 300, dent portion 310 and projection portion 320 are formed so as to respectively engage with projection portion Rd and dent portion Rc of the rack set in rack set unit 300. The upper surfaces of projection portions 311 to the right and left of dent portion 310 are lower than the upper surface of drawer 30, and the upper surface of projection portion 320 is higher than the upper surface of drawer 30. Also, projection portion 330 is formed in the center of rack set unit 300. Gaps 331 to 333 corresponding to three projection portions Re of the rack set in rack set unit 300 are formed in projection portion 330.

FIG. 5C is a diagram illustrating the case where rack set unit 300 taken out by C1-C2 in FIG. 5B is seen from front thereof (in the Y-axis positive direction).

In projection portion 330, transmission sensors 341 to 343 are provided to sandwich gaps 331 to 333 therebetween. For example, when rack R1 is set in rack set unit 300, three projection portions Re formed in rack R1 are positioned in gaps 331 to 333. Accordingly, when it is detected by detection signals of sensors 341 to 343 that projection portion Re is positioned in at least one of gaps 331 to 333, it is recognized that the rack is set in rack set unit 300. Also, hard disk 270 (see, FIG. 8) in main body 2 stores the configuration of projection portion Re of racks R1 to R6 illustrated in FIGS. 4A to 4F. With this, the rack set in rack set unit 300 may be identified as one of racks R1 to R6.

Also, when the rack is placed in rack set unit 300 so as to reverse the back and forth directions, the bottom surface of the rack including projection portion Rd and dent portion Rc comes in contact with projection portions 311, 320, which causes the rack to tilt in the back and forth directions. Accordingly, the operator may realize that the placement direction of the rack is wrong. It is to be noted in the embodiment that even when the rack is placed so as to reverse the back and forth directions, projection portion Re and rack set unit 300 are configured so as not to bring projection portion Re into contact with projection portion 330.

Return to FIG. 2. When the rack is set in drawer 30 and drawer is pushed backwardly, flange portion 31 provided behind drawer 30 is positioned in a gap between transmission sensors 41 provided in case 2a. Accordingly, it is recognized with detection signals of sensors 41 that drawer 30 is pulled out or that drawer 30 is pushed and closed. After that, bar member 32 provided in drawer 30 is driven in the Y-axis direction by an unillustrated driver and is inserted into holes 42 provided in case 2a to be locked, so that drawer 30 is prevented from being wrongly drawn. Also, bar member 32 is driven in a direction opposite to the lock direction, so that the lock of drawer 30 is released.

When processing is started on the sample tubes held in the rack, the sample tubes in holding positions n1 to n10 are sequentially taken out by tube transfer unit 50 from the rack and are transferred. Tube transfer unit 50 includes motors 51, 52, belts 53, 54, and movement body 500.

Movement body 500 includes right-left movement unit 510, front-back movement unit 520, up-down movement unit 530, and holder 540. Right-left movement unit 510 is movable in the right and left directions while being supported by a guide (unillustrated), which is provided in case 2a and extends in the right and left directions. Front-back movement unit 520 is movable in the back and forth directions while being supported by a guide (unillustrated) which is provided in right-left movement unit 510 and extends in the back and forth directions. Up-down movement unit 530 is moved relative to front-back movement unit 520 in the up and down directions by a cylinder (unillustrated) provided in front-back movement unit 520. Holders 540 are configured to be capable of holding sample tubes T1 to T3 between the back and forth directions, and are supported by up-down movement unit 530 to be rotatable about the Y-axis as a rotation axis.

Motor 51 drives belt 53 installed around pulleys provided on the right and left sides of case 2a in the right and left directions. Attachment stay 511 of right-left movement unit 510 is fixed in the belt 53. Accordingly, the right-left movement unit 510 becomes movable in the right and left directions along with the belt 53. Motor 52 drives belt 54 installed in pulleys provided on the right and left sides of case 2a in the right and left directions. One portion of belt 54 is forwardly folded by pulleys 512 provided in right-left movement unit 510 and is installed on the pulleys 513 provided in the front side of right-left movement unit 510. Attachment stay 521 of front-back movement unit 520 is fixed in belt 54 between pulleys 512, 513. Accordingly, front-back movement unit 520 becomes movable in the back and forth directions along with belt 54. Thus, holders 540 become freely movable in the X, Y, and Z directions in case 2a.

Stirrer mechanism 60 includes motor 61, shaft 62 which is connected with motor 61 and extends in the Y-axis direction, and abutting member 63 fixed in shaft 62. The sample tube which is held by grippers 541, 542 and is positioned in position P1 is pushed by abutting member 63 and is turned down, so that a sample inside the sample tube is stirred.

Figure 6B:
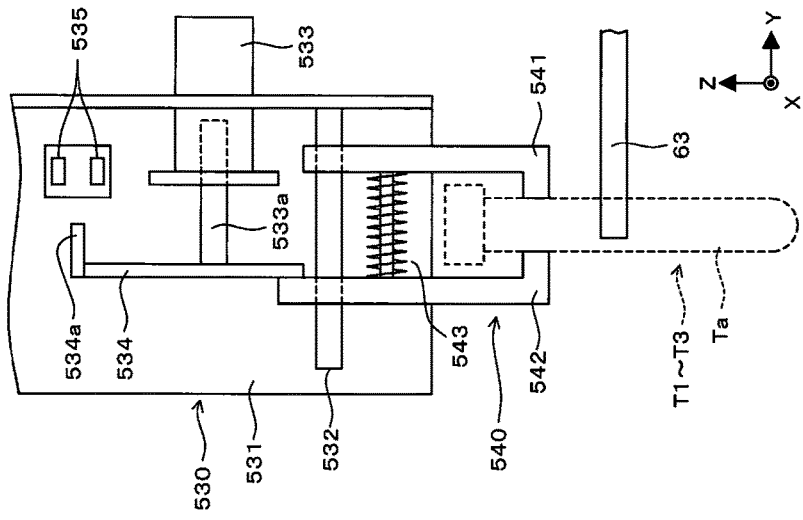
FIGS. 6A and 6B are schematic diagrams, each illustrating a case where a vertical movement unit, holder, and stirrer mechanism are seen in the X-axis negative direction.
Figure 6A:
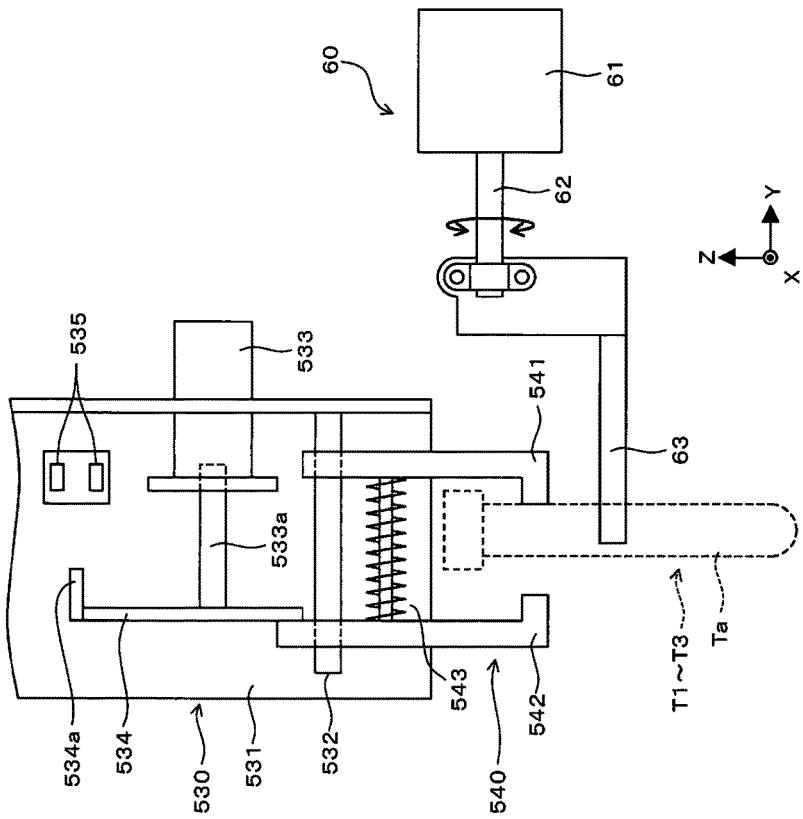

FIGS. 6A and 6B schematic diagrams, each illustrating the case where up-down movement unit 530, holder 540, and stirrer mechanism 60 are seen in the X-axis direction.

Up-down movement unit 530 includes base board 531, shaft 532 fixed to base board 531, cylinder 533 fixed to base board 531, plate member 534 provided in an end portion on the Y-axis negative side of rod 533a of cylinder 533, flange portion 534a provided in an upper end of plate member 534, and transmission sensors 535 provided in base board 531 on the Y-axis positive side of flange portion 534a.

Holder 540 includes grippers 541, 542 provided in shaft 532 to be rotatable about shaft 532 as a rotation axis, and spring 543 provided between grippers 541, 542. Gripper 541 is provided in shaft 532 so as not to move in the Y-axis direction, and the upper end of gripper 542 is positioned on the Y-axis negative side of plate member 534.

When force is not added to rod 533a in the Y-axis negative direction, gripper 542 is pulled in the Y-axis positive direction with contractible force of spring 543 and the lower ends of grippers 541, 542 come in contact with each other. At this time, plate member 534 is pushed in the Y-axis positive direction by the upper end of gripper 542 and flange portion 534a is positioned in the gap between sensors 535. Accordingly, it is detected that the lower ends of grippers 541, 542 come in contact with each other, that is, the sample tube is not gripped by holder 540.

When cylinder 533 pushes rod 533a in the Y-axis negative direction, as illustrated in FIG. 6A, plate member 534 moves in the Y-axis negative direction. At this time, plate member 534 pushes the upper end of gripper 542 in the Y-axis negative direction with contractile force of spring 543, and flange portion 534a moves in the Y-axis negative direction of sensor 535.

In order for grippers 541, 542 to grip sample tubes T1 to T3, grippers 541, 542 are firstly moved to the position of the sample tube (rack holding position) to be gripped in a state where grippers 541, 542 are opened, and lowered to a position at a predetermined height as illustrated in FIG. 6A. Then, when the force of cylinder 533 to push rod 533a is weakened, gripper 542 moves in the Y-axis positive direction, and body portion Ta of the sample tube is gripped by grippers 541, 542 with the contractile force of spring 543 as illustrated in FIG. 6B. Since the sample tube is between grippers 541, 542 at that time, gripper 542 stops at a predetermined position and flange portion 534a is not positioned in the gap between sensors 535. Accordingly, it is detected that the holder 540 grips the sample tube.

When the sample tube is transferred by tube transfer unit 50 to position P1 illustrated in FIG. 2, the sample tube is turned down by stirrer mechanism 60 in this position. Specifically, when motor 61 rotates shaft 62, the front end of abutting member 63 moves in the X-Z plane along an arch having shaft 62 at the center. Accordingly, body portion Ta of the sample tube is pushed from the X-axis negative side by abutting member 63. When the sample tube is returned to the vertical state, motor 61 rotates shaft 62 in the reverse direction and abutting member 63 is separated from the sample tube. Accordingly, grippers 541, 542 gripping the sample tube are returned to the vertical state with the weights thereof.

Return to FIG. 2. When stirring processing by stirrer mechanism 60 is terminated in position P1, this sample tube is set by tube transfer unit 50 in tube set unit 71 of back-and-forth conveyance unit 70 positioned in position P2. Back-and-forth conveyance unit 70 includes tube set unit 71 which is capable of holding the sample tube and motor 72 to move tube set unit 71 in the back and forth directions.

The sample tube set in tube set unit 71 in position P2 is conveyed to position P3 by tube set unit 71. When the sample tube is positioned in position P3, barcode reader 82 provided near position P3 reads sample ID from barcode label Tc adhered to the sample tube. Then, the sample tube is conveyed to position P4 by tube set unit 71. When the sample tube is positioned in position P4, a predetermined amount of sample is aspirated by sample aspiration unit 210 from the sample tube via piercer 211. Sample aspiration unit 210 includes piercer 211 to aspiration the sample in the sample tube and motor 212 with a stepping motor to drive piercer 211 in the up and down directions.

When aspiration of the sample is terminated, this sample tube is conveyed to the front of tube set unit 71 and is positioned in position P2. Then, this sample tube is returned to the original rack holding position by tube transfer unit 50. In this manner, the sample tubes held in the rack are sequentially taken out and sample aspiration unit 210 aspirations the sample.

The sample aspirated through piercer 211 is discharged to sample preparation unit 220. Sample preparation unit 220 mixes the sample with a reagent and the mixed solution is heated to prepare a measurement sample. The prepared measurement sample is supplied to detector 230. Detector 230 acquires various kinds of signals by emitting laser beams to the measurement sample. The acquired measurement result is analyzed by CPU 201 (see, FIG. 8) and the analysis result is displayed in display input unit 3.

When the analysis of one sample is preferentially performed (in the case of the manual processing), the operator stirs the sample in the sample tube in advance. The operator opens door 23 and sets this sample tube in tube set unit 71 positioned in position P5 (see, FIG. 2), and then pushes start button 83. This sample tube is conveyed to the back of tube set unit 71. Then, barcode reader 82 reads sample ID, and the sample is aspirated. After that, this sample tube is positioned by tube set unit 71 in position P5, and the operator opens door 23 to take out the sample tube from case 2a.

FIG. 7A is a diagram illustrating stirring processing by stirrer mechanism 60. FIGS. 7B to 7D are diagram, each illustrating the aspiration processing by sample aspiration unit 210. FIG. 7E is a conceptual diagram illustrating a setting table configuration stored in hard disk 270 (see, FIG. 8) in main body 2.

Refer to FIG. 7A. When a turned-down operation in which a sample tube is returned from the vertical state to the vertical state after the turned-down state is counted as one, the numbers of turning down the sample tubes T1 to T3 are respectively set to fn1, fn1, and fn2 as indicated in the setting table in FIG. 7E. Here, fn1<fn2. Accordingly, the sample in sample tube T3 whose capacity is smaller than those of sample tubes T1 and T2 can be sufficiently stirred.

Now refer to FIGS. 7B to 7D. In order to lower piercer 211 to the sample tube, the lower end of piercer 211 is aligned with the initial position, and then motor 212 is given a predetermined number of pulses and accordingly lowers piercer 211. In this process, the number of pulses given to motor 212 is set to pn1, pn2, and pn3 for sample tubes T1 to T3, respectively, as indicated in the setting table in FIG. 7E so that a lowering amount becomes suitable. Here, pn1>pn2>pn3. Accordingly, piercer 211 can be properly lowered according to the height of bottom surfaces Td of sample tubes T1 to T3.

Figure 8:
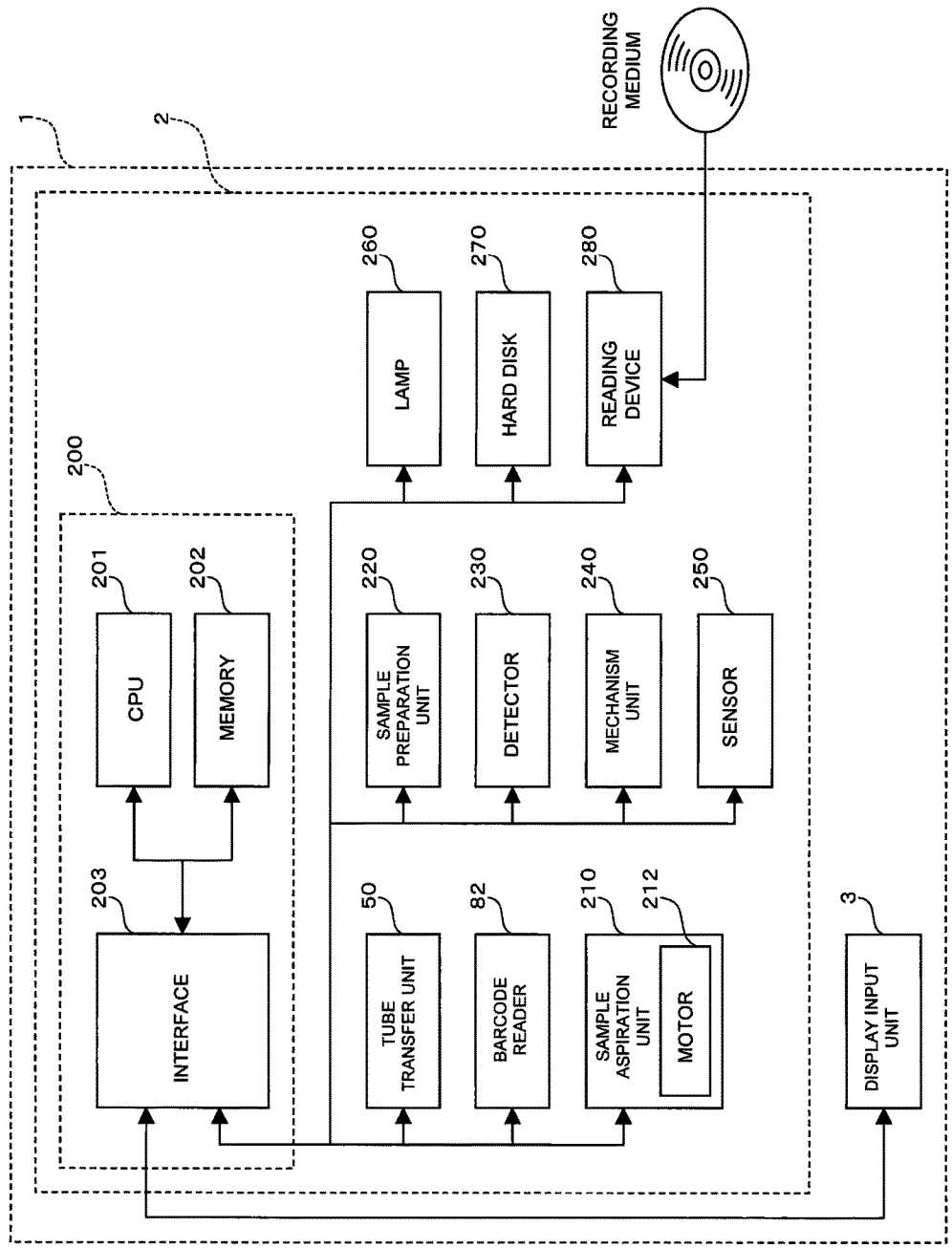
FIG. 8 is a block diagram illustrating a configuration of the sample analyzer according to the embodiment.

FIG. 8 is a block diagram illustrating the configuration of sample analyzer 1.

Main body 2 includes substrate 200, mechanism unit 240, sensor unit 250, lamp unit 260, hard disk 270, and read device 280 in addition to above-described tube transfer unit 50, barcode reader 82, sample aspiration unit 210, sample preparation unit 220, and detector 230. Substrate 200 includes CPU 201, memory 202, and interface 203.

CPU 201 executes computer programs stored in memory 202 and computer programs loaded in memory 202. CPU 201 controls the units of main body 2 and display input unit 3 and receives signals from the units of main body 2 and display input unit 3, through interface 203.

Mechanism unit 240 includes a mechanism to drive the units of main body 2. Sensor unit 250 includes a sensor to detect that door 23 is closed and a sensor to detect that power button 11, start buttons 12, 83, or stop button 13 is pressed, in addition to above-described two sensors 41, 81 and 341 to 343, 535. Lamp unit 260 includes two lamps 22.

Hard disk 270 stores an operating system, computer programs which are executed by CPU 201, the configuration of projection portions Re of racks R1 to R6, the setting table in FIG. 7E, and management information to be described later. Read device 280 includes a CD drive, DVD drive, or the like, and can read out computer programs and data, which are stored in the recording medium.

Figure 9B:
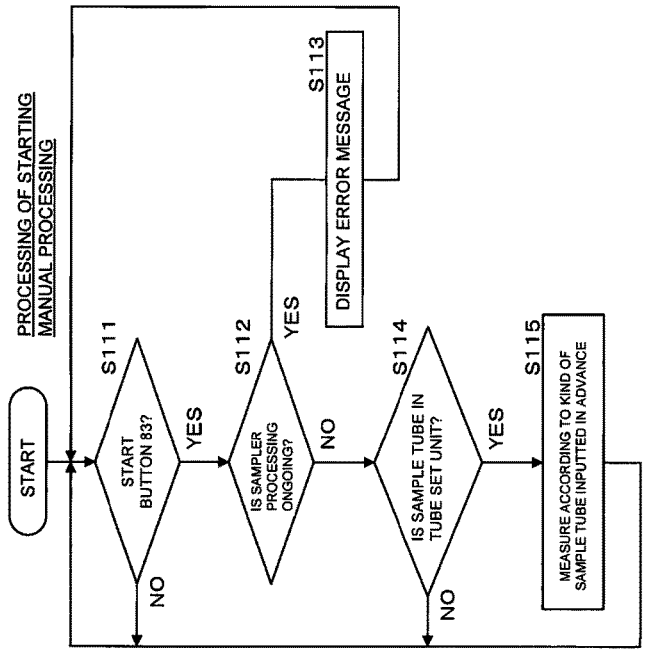
FIGS. 9A and 9B are flowchart respectively illustrating processing of starting and suspending sampler processing and processing of starting manual processing according to the embodiment.
Figure 9A:
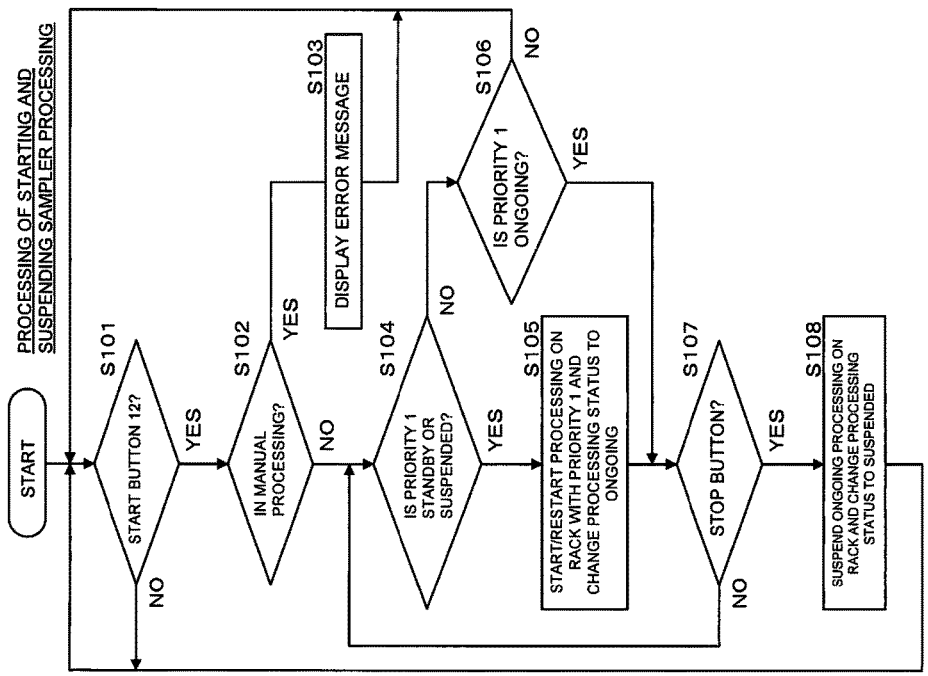

FIG. 9A is a flowchart illustrating processing of starting and suspending sampler processing which is performed by CPU 201.

When an operator presses power button 11 to turn on sample analyzer 1, CPU 201 determines whether or not start button 12 is pressed (S101) and positions tube set unit 71 in position P5. When start button 12 is pressed (S101: YES), CPU 201 determines whether or not the manual processing (S112 to S115 in FIG. 9B) is performed (S102). When the manual processing is performed (S102: YES), CPU 201 displays an error message indicating that sampler processing is not possible on display input unit 3 (S103), the process is returned to S101. On the other hand, when the manual processing is not performed (S102: NO), CPU 201 performs processing on the rack.

Here, hard disk 270 stores management information indicating status of the units of sample analyzer 1 and the like. The management information includes information indicating that processing is firstly performed on a rack, among the racks set in two drawers 30, the kinds of the set racks, and processing statuses of the set racks. The management information is registered at S206 in FIG. 10. The management information registering processing is described later by referring to FIG. 11.

Referring to the management information, CPU 201 determines whether or not the rack with the highest processing priority (priority 1) is in the standby or suspended status (S104). When the rack with priority 1 is in the standby or suspended status (S104: YES), CPU 201 starts or restarts the processing on the rack with priority 1 and changes the processing status of this rack to ongoing (S105). Here, the suspended processing of the rack is restarted from the suspended state.

The rack with priority 1 is in the standby or suspended status, and but in the ongoing status (S104: NO, S106: YES), S105 is skipped. On the other hand, when the rack with priority 1 is out of the standby, suspended and ongoing statuses (S104: NO, S106: NO), there is no rack to be processed, and the process is returned to S101.

After that, CPU 201 determines whether or not stop button 13 is pressed (S107). When stop button 13 is not pressed (S107: NO), the process is returned to S104. On the other hand, when stop button 13 is pressed (S107: YES), CPU 201 suspends the ongoing processing on the rack and changes the processing status of this rack to suspended (S108). Then, CPU 201 returns the process to S101.

FIG. 9B is a flowchart illustrating processing of starting the manual processing by CPU 201. This processing is performed in parallel with processing in FIG. 9A.

When the operator presses power button 11 and power of sample analyzer 1 is turned on, CPU 201 determines whether or not start button 83 is pressed (S111). When start button 83 is pressed (S111: YES), CPU 201 determines whether or not sampler processing (S102 to S108 in FIG. 9A) is performed (S112). When the sampler processing is performed (S112: YES), CPU 201 displays an error message indicating that the manual processing is not possible (S113), on display input unit 3, and returns the process to S111. It is to be noted that instead of displaying the error message on display input unit 3, an alarm sound may be outputted from a speaker (unillustrated) in main body 2. On the other hand, when the sampler processing is not performed (S112: NO), CPU 201 moves tube set unit 71 to the position of sensor 81 (see FIG. 2), and determines based on the detection signals of sensor 81 whether or not the sample tube is set in tube set unit 71 (S114).

When the operator desires to preferentially perform measurement on one sample tube, the operator inputs the kind of this sample tube, in other words, sample tube T1, T2, or T3 in display input unit 3 in advance. After that, the operator sets the sample tube in tube set unit 71 and presses start button 83. In this manner, when the sample tube is set in tube set unit 71 by the operator (S114: YES), CPU 201 performs measurement according the kind of the sample tube, which is inputted in advance (S115). On the other hand, when no sample tube is set in tube set unit 71 (S114: NO), CPU 201 returns the process to S111. It is to be noted that when an error message is displayed at S113, the operator presses stop button 13 to suspend the sampler processing and presses again start button 83 to continue the manual processing.

Figure 10:
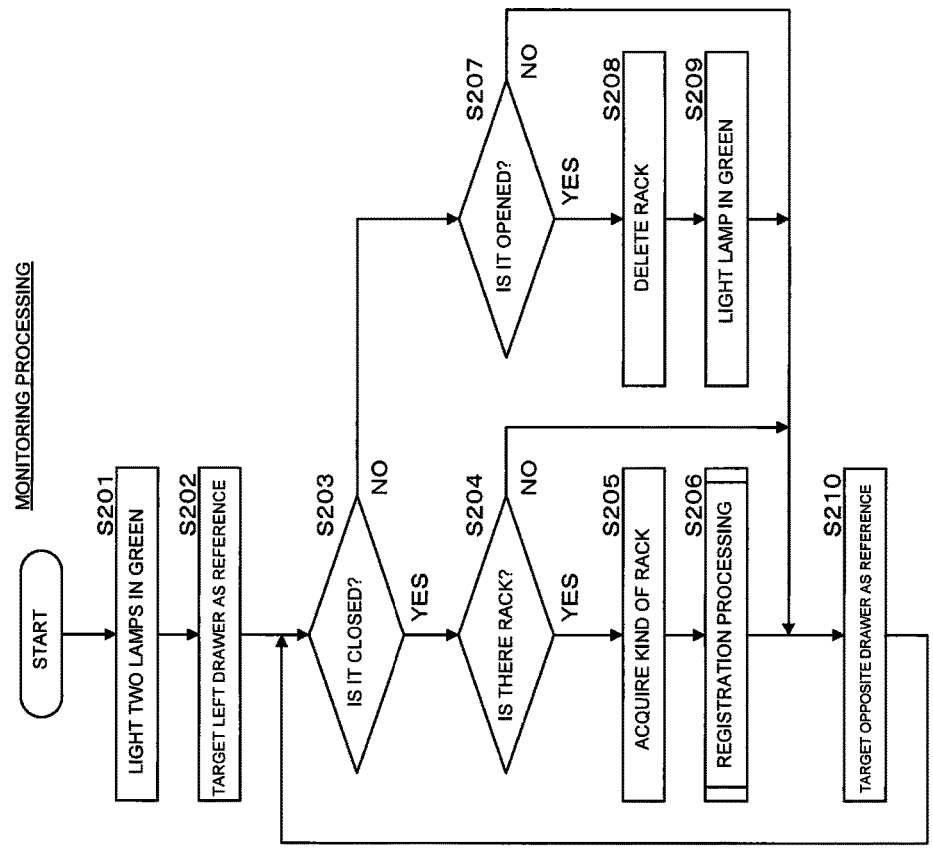
FIG. 10 is a flowchart illustrating monitoring processing according to the embodiment.

FIG. 10 is a flowchart illustrating monitoring processing by CPU 201. This processing is performed in parallel with processing in FIG. 9A.

When the operator presses power button 11 and sample analyzer 1 is powered on, CPU 201 lights two lamps 22 in green (S201), and sets drawer 30 on the left side of two drawers 30 as a reference target (S202). Then, CPU 201 determines based on detection signal of sensor 41 whether drawer 30 is closed or opened (S203, S207).

When reference target drawer 30 is closed (S203: YES), CPU 201 determines based on detection signals of sensors 341 to 343 whether or not the rack is in this drawer 30 (S204). When the rack is in this drawer 30 (S204: YES), CPU 201 acquires the kind of this rack, in other words, that this rack is which one of racks R1 to R6, from the configuration of projection portions Re (S205). After that, CPU 201 performs "registering processing" (S206). The registering processing is described later by referring to FIG. 11. When the rack is not in this drawer 30 (S204: NO), the process proceeds to S210.

When reference target drawer 30 is opened (S203: NO, S207: YES), CPU 201 deletes the information on the rack, which is stored in the management information, in reference target drawer 30 (s208). In other words, when this drawer 30 is opened before the processing on the rack in drawer 30 starts, the information on the rack is deleted from the management information. It is to be noted that in a case where this rack is registered as a rack with priority 1 and there is another rack whose priority of processing is registered as the second (hereinafter, referred to as "priority 2"), the rack with priority 2 is raised up to the rack with priority 1.

Then, CPU 201 lights lamp 22 above this drawer 30 in green (S209). In other words, when the processing on the rack in drawer 30 is completed, lamp 22 is not lit as described later. At S209, lamp 22 that is not lit is lit in green.

On the other hand, when reference target drawer 30 is not opened or closed (S203: NO, S207: NO), the process proceeds to S210.

Next, CPU 201 returns process to S203 by using drawer 30 on the opposite side of reference target drawer 30 as a reference target (S210). In this manner, processes at S203 to S210 are repeatedly performed at a predetermined time interval.

Figure 11:
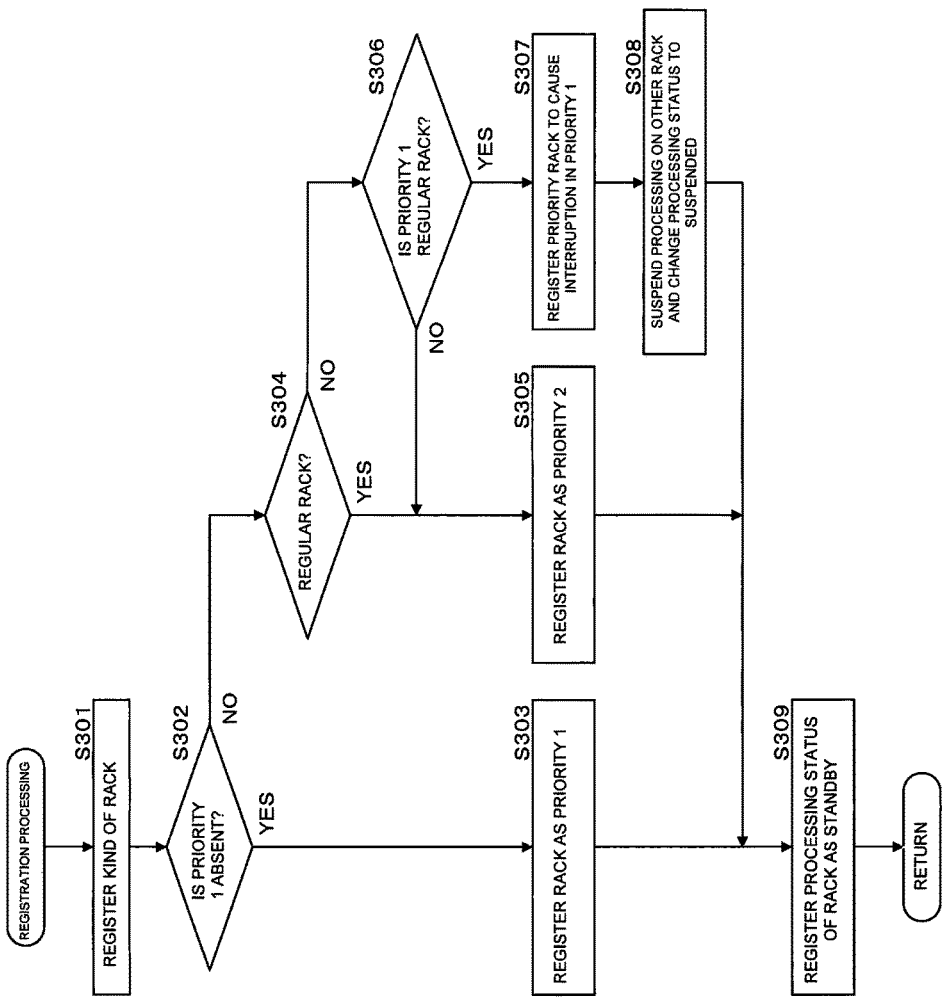
FIG. 11 is a flowchart illustrating registering processing according to the embodiment.

FIG. 11 is a flowchart illustrating the registering processing.

CPU 201 registers the kind of the rack acquired at S205 in the management information (S301). Subsequently, CPU 201 refers to the management information and then determines whether or not there is already another rack with priority 1 (S301). When there is no rack with priority 1 (S302: YES), CPU 201 registers a regular rack in reference target drawer 30 as a rack with priority 1 (S303). On the other hand, when there is a rack with priority 1 (S302: NO), CPU 201 determines whether or not a regular the rack set in reference target drawer 30 is a regular rack (S304).

When the rack in reference target drawer 30 is a regular rack (S304: YES), CPU 201 registers this regular rack as a rack whose priority of processing is the second in the management information (S305). On the other hand, when the rack in reference target drawer 30 is not a regular rack, in other words, a priority rack (S304: NO), CPU 201 determines whether or not the rack with priority 1 is a regular rack (S306).

When the rack with priority 1 is not a regular rack, in other words, a priority rack (S306: NO), CPU 201 registers the priority rack in reference target drawer 30 as a rack with priority 2 in the management information (S305). On the other hand, when the rack with priority 1 is a regular rack (S306: YES), CPU 201 inserts the priority rack in reference target drawer 30 to interrupt the regular rack with priority 1 and registers the priority rack as priority 1 in the management information (S307). Accordingly, the regular rack with priority 1 is moved to priority 2. When the regular rack is in the ongoing status, CPU 201 suspends the processing on the regular rack, and changes the processing status of the regular rack to suspended (S308).

Next, CPU 201 registers the processing status of the rack in reference target drawer 30 in the management information as suspended (S309). Then, the registering processing is terminated. It is to be noted that processing on the rack whose priority is determined at S304, S306 as 1 is started at S105 in FIG. 9A. Also, the rack whose priority is determined at S305 as 2 is waited until the rack with priority 1 is deleted from the management information.

Figure 12A:
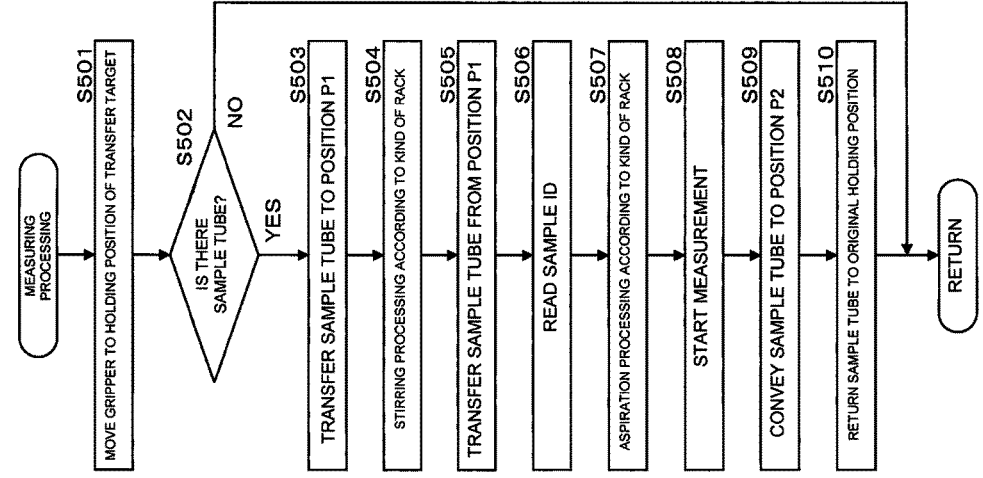
FIG. 12A is a flowchart illustrating processing on the rack according to the embodiment.

FIG. 12A is a flowchart illustrating processing which is performed by CPU 201 on a rack. This processing is started at S105 in FIG. 9A and independently performed on each rack.

CPU 201 lights lamp 22 in green above drawer 30 in which a processing target rack is set and locks this drawer 30 (S401). Subsequently, CPU 201 performs "measuring processing" (S402).

Figure 12B:
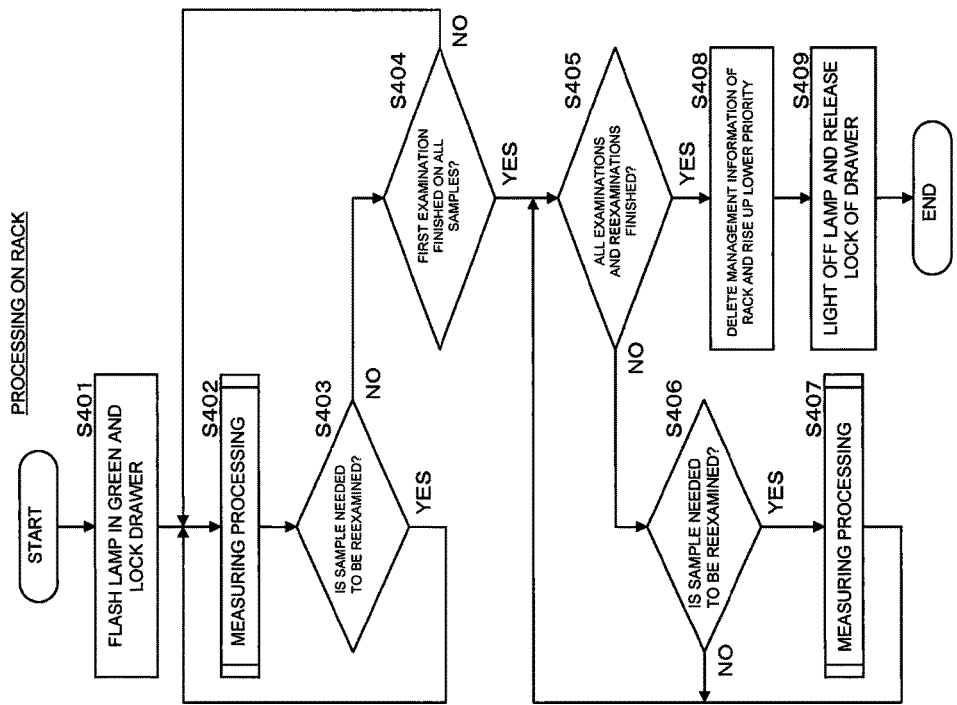
FIG. 12B is a flowchart illustrating measuring processing according to the embodiment.

FIG. 12B is a flowchart illustrating the measuring processing.

CPU 201 moves grippers 541, 542 above the holding position to be a transfer target (S501). It is to be noted that the holding position to be a transfer target is set in any of rack holding positions n1 to n10. The first transfer target is holding position n1, and every time the measuring processing is performed on this rack, the holding position sequentially moves from holding position n2 to n10.

Subsequently, CPU 201 causes tube transfer unit 50 to perform an operation to grip the sample tube described by referring to FIGS. 6A and 6B and determines whether or not the sample tube is in this holding position (S502). When the sample tube is not in this holding position (S502: NO), the measuring processing is terminated. When the sample tube is in this holding position (S502: YES), CPU 201 causes tube transfer unit 50 to transfer the sample tube to position P1 (S503).

Next, by referring to the setting table in FIG. 7E, CPU 201 drives stirrer mechanism 60 to perform stirring processing on the sample tube positioned in position P1 according to the kind of a rack to be a processing target (S504). Then, CPU 201 causes tube transfer unit 50 to transfer the sample tube from position P1 to position P2 and sets the sample tube in tube set unit 71 positioned in position P2 (S505). After that, CPU 201 conveys the sample tube to position P3 and reads sample ID with barcode reader 82 (S506), and further conveys the sample tube to position P4. Then, by referring to the setting table, CPU 201 drives sample aspiration unit 210 to perform aspiration processing on the sample tube positioned in position P4 according to the kind of the processing target rack (S507).

Subsequently, CPU 201 starts measurement on the aspirated sample (S508). Accordingly, a measurement sample is prepared from the aspirated sample, which is measured by detector 230. After that, CPU 201 determines based on the obtained measurement result whether or not the sample held in the sample tube requires to be reexamined. It is to be noted that measurement started at S508 and determination whether or not reexamination is needed are performed in parallel with other processing.

Next, CPU 201 conveys the sample tube to position P2 (S509), and the sample tube positioned by tube transfer unit 50 in position P2 is returned to the original holding position of the original rack (S510). In this manner, the measuring processing is terminated.

It is to be noted that when tube transfer unit 50 transfers sample tubes in holding positions in the front row (holding positions n1 to n5), a space formed by center portion Rb of the rack is used for transfer. Accordingly, compactly-configured tube transfer unit 50 can smoothly transfer sample tubes. Also, tube transfer unit 50 transfers the sample tube so that the sample tube does not pass through the front side of rack set unit 300 of drawer 30. This allows the operator to draw out drawer 30 on the opposite side of the drawer 30 in which the processing target rack is set.

Return to FIG. 12A. When the measuring processing is terminated, CPU 201 determines whether or not the processing target rack includes a sample, which needs to be reexamined (S403). When there is a sample which needs to be reexamined (S403: YES), the process returns to S402 and the measuring processing is performed again on the sample which is determined that reexamination is needed.

When there is no sample, which is needed to be reexamined (S403: NO), CPU 201 determines whether or not first examination is terminated on all the samples (S404). When the first examination is not terminated on all the samples (S404: NO), the process is returned to S402 and the measuring processing on the next sample tube is performed. On the other hand, when the first examination is terminated on all the samples (S404: YES), CPU 201 determines whether or not reexamination determination on all the samples and all the necessary reexaminations are terminated (S405). In a case where all the reexamination determinations and reexaminations are not terminated (S405: NO), CPU 201, when there is a sample which needs to be reexamined (S406: YES), the measuring processing is performed on this sample as similar to S402 (S407). When all the reexamination determinations and the necessary reexaminations are terminated (S405: YES), the process is continued to S408.

Next, CPU 201 deletes the information on the processing target rack from the management information (S408). When there is a rack with priority 2 at this time, CPU 201 raises up the priority of this rack to priority 1. Subsequently, CPU 201 lights off lamp 22 above drawer 30 in which the processing target rack is set and release the lock of drawer 30. In this manner, the processing on the rack is terminated.

If the processing on the rack being performed is suspended at S108 in FIG. 9A, the processing is suspended at the measuring processing at S402, S407. Specifically, in the measuring processing in FIG. 12B, the transfer target sample tube is returned to the original holding position of the original rack if the processing on the rack is suspended before the aspiration processing at S507 is started, the measuring processing is returned to S501 and suspended. If the processing on the rack is suspended after the aspiration processing at S507 is started, the measuring processing already started is continued until end, and the measuring processing is suspended just before the measuring processing is performed on the next sample tube.

As described above, according to the embodiment, the kind of a rack is detected when the rack is set in rack set unit 300 in drawer 30. Then, operations of tube transfer unit 50 and the like are controlled according to the detected kind of the rack. For this reason, a complex input operation to input the information on which one of the six kinds of sample tubes is set for each sample tube through display input unit 3 can be omitted. Accordingly, a complex input operation by an operator can be simplified.

Also, according to the embodiment, the rack has projection portions Re formed therein according to the kinds of the sample tubes held in the rack. Then, when the rack is set in rack set unit 300, the kind of the rack is detected based on the projection portion Re. In this manner, the kind of the rack is detected based on the shape of the rack. Accordingly, for example, providing a large detection mechanism such as a barcode reader is not needed. Thus, the complex input operation by an operator can be simplified and the cost of sample analyzer 1 can be lowered.

In the embodiment, a barcode label or a RFID tag including the information on the kind of the rack may be adhered to the rack in place of the projection portions Re. In this case, a barcode reader to read barcode information or an antenna to read the RFID is provided inside case 2a. In addition, in place of projection portions Re, colors may be set for racks according to kinds of the racks. In this case, a color sensor to read the colors of the racks is provided inside case 2a. Also in this case, as long as an operation of tube transfer unit 50 is controlled based on the acquired kinds of the racks, even in the case where projection portions Re are used, the complex input operation by an operator may be simplified. However, for example, when a barcode label is adhered to the rack, it is possibly caused that the rack is not identified because a barcode is broken or becomes dirty or a maintenance work to change an aging barcode label becomes necessary. Also, in these cases, a barcode reader, an antenna, or a color sensor have to be provided additionally. Accordingly, the cost of sample analyzer 1 may increase. Thus, it is preferable that the kinds of the racks be detected according the shapes (projection portions Re) of the racks as described in the embodiment.

Also, according to the embodiment, projection portions Re are formed on the lower surface side of the rack to face rack set unit 300. Accordingly, sensors 341 to 343 of rack set unit 300 can detect a kind of a rack in response to operation work of setting the rack into rack set unit 300.

Also, according to the embodiment, when a rack is set in rack set unit 300, projection portions Re of the rack are positioned in gaps 331 to 333. At this time, the translucent state and light-shielding state of sensors 341 to 343 change depending on whether or not there are projection portions Re, and thus it can be identified based on the detection signals of sensors 341 to 343 that the set rack is which one of racks R1 to R6. In this manner, the kind of the rack can be specified with a simple configuration by only providing projection portions Re, so that the rack can be formed with a simple structure.

Also, according to the embodiment, there are three positions where projection portions Re are to be formed, and projection portion Re is formed in at least one of the three positions to make it possible to determine whether or not the rack is set. Thus, there are seven different combinations of arrangement of projection portions Re. Also, projection portions Re are detected by sensors 341 to 343. In this manner, since the kind of the rack is identified based on the combinations of arrangement of projection portions Re detected by sensors, the number of projection portions Re and sensors to detect projection portions Re can be curbed. Thus, the configuration of the rack and the sensor can be simplified.

Also, according to the embodiment, drawer 30 moves back and forth as illustrated in FIG. 5A, so that rack set unit 300 moves between a loaded position inside case 2a and a drawn position outside case 2a. Thereby, the rack is set smoothly in a detachably-attached manner in rack set unit 300.

Also, in the embodiment, sensors 341 to 343 are provided in projection portion 330. In this manner, when sensors 341 to 343 are integrally provided with drawers 30, the kind of the rack can be identified even in the state where drawer 30 is drawn out to the outside from case 2a.

In addition, according to the embodiment, the rack is provided with recessed portions Rc and projection portions Rd and rack set unit 300 is provided with dent portions 310 and projection portions 320. Then, when the rack is set in rack set unit 300, recessed portions Rc and projection portions 320 are engaged with each other and projection portions Rd and dent portions 310 are engaged with each other. Accordingly, the rack can be set in rack set unit 300 in a proper posture and projection portions Re can be properly detected by sensors 341 to 343.

Figure 13A:
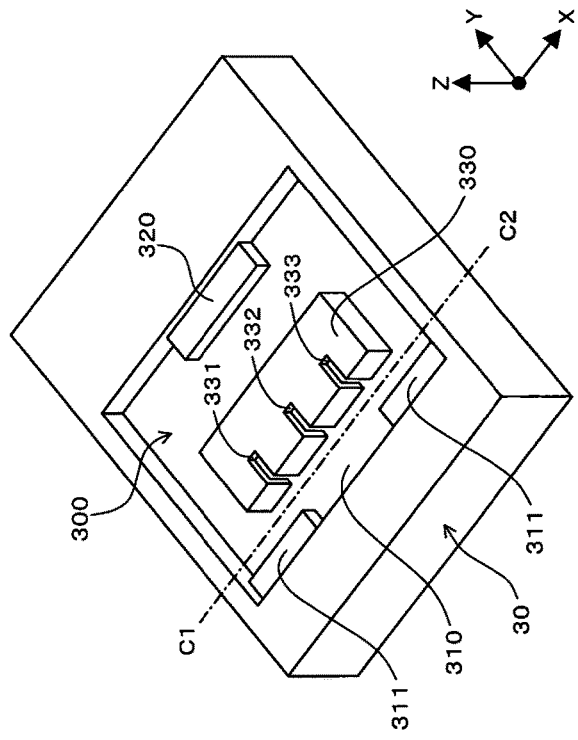
FIG. 13A is a diagram illustrating a configuration of a drawer according to the embodiment.
Figure 13B:
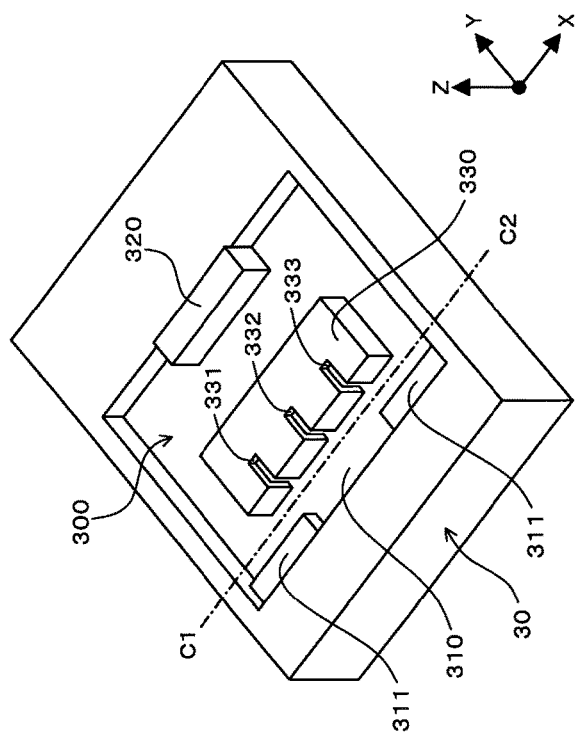
FIG. 13B is a diagram illustrating a modified embodiment of the configuration of the drawer according to the embodiment.

In addition, according to the embodiment, as illustrated in FIG. 13 again, the upper surface of projection portion 311 is lower than the upper surface of drawer 30 and the upper surface of projection portion 320 is higher than the upper surface of drawer 30. Accordingly, when the rack is placed in rack set unit 300 reversely in the back and front, the rack tilts, so that it can be noticed that the placement direction of the rack is wrong. It is to be noted that as illustrated in FIG. 13B that the upper surface of projection portion 320 may be positioned in the same height as that of the upper surface of projection portion 311. In this case, when the rack is placed in rack set unit 300 reversely in the back and front, although the rack is not properly mounted in rack set unit 300, a lower portion of the rack is shallowly engaged with rack set unit 300 and the rack does not tilt in this state. For this reason, it becomes difficult for an operator to notice that the placement direction of the rack is wrong. Accordingly, it is preferable that the upper surface of projection portion 320 be higher than the upper surface of rack set unit 300 as illustrated in FIG. 13A.

As described above, since the lower portion of the rack has asymmetric contour in the plan view, this power portion is engaged with rack set unit 300 from above, so that the rack can be properly set in rack set unit 300 in a proper posture. Accordingly, projection portions Re can be properly detected by sensors 341 to 343.

Also, according to the embodiment, two drawers 30 are provided so as to be side by side and sensors 341 to 343 are respectively provided in two drawers 30. Accordingly, different kinds of racks can be respectively set in two rack set units 300, so that convenience can be improved. Also, even when sensors 341 to 343 configured to detect projection portions Re are respectively provided in two rack set units 300, as compared with the case where a barcode reader is provided to acquire the kind of the rack by the barcode reader, the configuration can be simplified and the cost can be reduced.

Also, according to the embodiment, when the processing on the rack is ongoing and suspended, lamp 22 for this drawer 30 is lit in green, and drawer 30 is locked. Also, when the processing on the rack is terminated, lamp 22 for this drawer 30 is lit out and the lock of drawer 30 is released. Also, when the processing on the rack is not started or when the rack is not set in drawer 30, lamp 22 for this drawer 30 is lit in green and the lock of the rack is released. Accordingly, the rack can be set in corresponding drawer 30 when lamp 22 is lit in green and when lamp 22 is lit off. Also, since it can be seen by checking the state of lamp 22 that the rack can be set in corresponding drawer 30, the rack can be smoothly set or exchanged.

Also, according to the embodiment, when a priority rack is set in drawer 30 and the priority of a regular rack set in drawer 30 on the opposite side is 1, the priority rack is regarded as having priority 1 and the processing on the regular rack is suspended (S306 in FIG. 11). Accordingly, a priority sample can be processed preferentially over a regular sample. Also, since the rack can hold multiple sample tubes, even when there are multiple priority samples, these priority samples are held by one rack to be set in drawer 30, so that multiple priority samples can be processed all together.

Also, according to the embodiment, by detecting the kind of the rack, it is possible to detect which of sample tubes T1 to T3 is held in the rack. Then, since the stirring processing suitable for the detected one of sample tubes T1 to 13 is executed based on the setting table, the sample in the sample tube can be surely stirred. In addition, the aspiration processing suitable for the detected one of sample tubes T1 to T3 is executed based on the setting table, so that the sample in the sample tube can be smoothly aspirated.

Also, according to the embodiment, the lower end of projection portion Re is positioned above the lower ends of racks R1 to R6. Accordingly, the racks can be stably placed on a workbench or the like.

Embodiments are described above. However, the invention is not limited to the embodiments, and further various modifications are possible as will be appreciated by a skilled artisan reader.

For example, in the above embodiment, a device to which the invention is applied is assumed to be sample analyzer 1 to analyze blood. However, it is not limited to this. The invention may be applied to a sample processing apparatus to perform processing on a sample, such as an immunity analyzer, gene amplification measurement device, biochemical analyzer, urine qualitative analyzer, in-urine physical component analyzer, or blood smear creation device.

Also, in the above embodiment, the rack is set in rack set unit 300 and drawer 30 is closed, so that the rack is accommodated in case 2a. However, it is not limited to this. A rack is directly set in case 2a, so that the rack is accommodated inside case 2a.

FIG. 14A is a schematic diagram illustrating that the rack is directly set in case 2a.

Panel 21 is configured to be closably openable by being upwardly pulled. Projection portion 610 is provided behind (the Y-axis positive direction) panel 21 incase 2a. As similar to projection portion 330 in the above-described embodiment, projection portion 610 has gaps 611 to 613 arranged in the vertical direction and is provided with transmission sensors (unillustrated) arranged to sandwich gaps 611 to 613 therebetween. Also, in this case, projection portions Re are provided on the rear side in the rack as in the above-described embodiment. Accordingly, like the above-described embodiment, the rack can be accommodated in case 2a and the kind of the rack can be identified based on detection signals of the sensors provided in projection portion 610.

Also, in the above-described embodiment, to identify kinds of racks set in rack set unit 300, projection portions Re to identify kinds of racks are provided in the rack. However, it is not limited to this. Other configuration to identify kinds may be provided in the rack. For example, in place of projection portions Re, cutouts are provided in the rack, and a limit switch corresponding to the cutout may be provided in projection portions 330. With this configuration, it is detected based on detection signals of the limit switch whether or not there is a cutout provided in the rack. Accordingly, as similar to the above-described embodiment, the kind of the rack can be identified.

Also, in the above-described embodiment, the state of drawer 30 is displayed by display of lamp 22. However, it may be always displayed by display input unit 3.

Also, in the above-described embodiment, the heights of sample tubes T1 to T3 are same and thus the height of gripping the sample tube by grippers 541, 542 is assumed to be same in any sample tube. However, when sample tubes with different heights are used, the height of gripping the sample tube may differ depending on the sample tubes. In this case, it is preferable that the position where grippers 541, 542 grip the sample tube be changed according to the length of the sample tube.

FIG. 14B is a drawing illustrating a grip position at which sample tubes T1 to T3 according to the above-described embodiment are gripped. In the above-described embodiment, sample tubes T1 to T3 are all gripped in a predetermined height position (for example, H1) by grippers 541, 542. On the other hand, FIG. 14C is a diagram illustrating the grip position at which sample tube T4 longer than sample tubes T1 to T3 is gripped. In this case, sample tube T4 is held by rack R7 with the configuration of projection portion Re different from those of racks R1 to R6, and is gripped by grippers 541, 542 at height position H2 above height position H1. Also, the setting table stores height position H1 for gripping sample tubes T1 to T3 and height position H2 for gripping sample tube T4.

With this configuration, even when sample tubes with different lengths are used, the sample tube can be used in an optimum grip position, so that a gripping state can be stabilized for each sample tube. Also, similarly, even when sample tubes with barrels Ta having different shapes are used, the gripping state can be stabilized for each sample tube. Also, in this case, there is no need to provide room in the length of grippers 541, 542 and the position of spring 543 so as not to bring spring 543 into contact with lid portion Tb. Thereby, tube transfer unit 50 can be made compact.

As described above, embodiments provide a sample processing apparatus and a rack that are capable of simplifying a complex input operation of an operator.

The invention claimed is:

1. A sample processing apparatus, comprising:
a case;
a rack with positions to hold sample tubes, the rack including a rack identification suited to a kind of sample tube;
a rack set unit that accepts the rack in a detachable manner;

a drawer that holds and moves the rack set unit between a loaded position in which the rack set unit is loaded in the case and a drawn position in which the rack set unit is drawn out from the case;

a tube transfer unit with mechanical movement to grab and take out each sample tube from a rack held in the rack set unit;

an aspiration unit that aspirates a sample in the sample tube;

a rack detector comprising a sensor to detect the rack identification of the rack held in the rack set unit; and a controller that controls an aspiration operation of the aspiration unit based on a detection result of the rack detector, wherein the rack detector is integrally provided with the drawer.

2. The sample processing apparatus according to claim 1, wherein the rack identification is arranged at a position distinctive for the kind of sample tube.

3. The sample processing apparatus according to claim 2, wherein the rack includes the rack identification on a lower surface side that faces the rack set unit.

4. The sample processing apparatus according to claim 2, wherein
the rack detector includes sensors, and
the rack detector detects the position of the rack identification based on a combination of detection results of the sensors.

5. The sample processing apparatus according to claim 1, wherein
the rack identification includes a projection shape, the rack set unit includes a gap into which the projection enters when the rack is set, and
the rack detector detects the projection shape entering the gap.

6. The sample processing apparatus according to claim 1, wherein the rack and the rack set unit comprise engagement portions, respectively, and the engagement portions position the rack in a predetermined set position by engaging with each other when the rack is mounted in the rack set unit.

7. A sample processing apparatus, comprising:
a rack with positions to hold sample tubes, the rack including a rack identification suited to a kind of sample tube;
two or more rack set units, each of the two or more rack set units detachably accepts the rack;
a tube transfer unit with mechanical movement to grab and take out each sample tube from a rack held in the rack set unit;
an aspiration unit that aspirates a sample in the sample tube;
a rack detector comprising a sensor to detect the rack identification of the rack held in the rack set unit; and
a controller that controls an aspiration operation of the aspiration unit based on a detection result of the rack detector,
wherein each rack set unit contains the rack detector.

8. The sample processing apparatus according to claim 7, further comprising a display unit, wherein
the controller causes the display unit to display which of the rack set units is available for setting the rack.

9. The sample processing apparatus according to claim 8, wherein
the display unit includes lights provided for the rack set units, respectively, and
the controller turns on a light for the rack set that is available for setting the rack in a first display mode, and turns on a light for the rack set unit which is not available for setting the rack in a second display mode different from the first display mode.

10. The sample processing apparatus according to claim 7, wherein
when a rack holding a priority sample is set in a first rack set unit while a rack holding a regular sample is already set in a second rack set unit, the controller directs the tube transfer unit to transfer sample tubes from the rack in the first rack set unit preferentially over the rack in the second rack set unit.

11. The sample processing apparatus according to claim 1, wherein
the tube transfer unit includes a gripper dimensioned to grip the sample tube when picking out the sample tube from the rack, and
the controller directs the gripper to change a grip position of the sample tube based on a detection result of the rack detector.

12. A sample processing apparatus, comprising:
a rack with positions to hold sample tubes, the rack including a rack identification suited to a kind of sample tube;
a rack set unit that accepts the rack in a detachable manner;
a tube transfer unit with mechanical movement to grab and take out each sample tube from a rack held in the rack set unit;
a rack detector comprising a sensor to detect the rack identification of the rack held in the rack set unit;
a stirrer mechanism that stirs a sample in the sample tube; and
a controller alters control of the stirrer mechanism to change a stirring condition based on a detection result of the rack detector.

13. The sample processing apparatus according to claim 7, wherein the rack identification is arranged at a position distinctive for the kind of sample tube.

14. The sample processing apparatus according to claim 7, wherein
the rack identification includes a projection shape, the rack set unit includes a gap into which the projection enters when the rack is set, and
the rack detector detects the projection shape entering the gap.

15. The sample processing apparatus according to claim 7, wherein the rack and the rack set unit comprise engagement portions, respectively, and the engagement portions position the rack in a predetermined set position by engaging with each other when the rack is mounted in the rack set unit.

16. The sample processing apparatus according to claim 12, wherein the rack identification is arranged at a position distinctive for the kind of sample tube.

17. The sample processing apparatus according to claim 16, wherein the rack includes the rack identification on a lower surface side that faces the rack set unit.

18. The sample processing apparatus according to claim 16, wherein
the rack detector includes sensors, and
the rack detector detects the position of the rack identification based on a combination of detection results of the sensors.

19. The sample processing apparatus according to claim 12, wherein
the rack identification includes a projection shape, the rack set unit includes a gap into which the projection enters when the rack is set, and the rack detector detects the projection shape entering the gap.

20. The sample processing apparatus according to claim 12, wherein the rack and the rack set unit comprise engagement portions, respectively, and the engagement portions position the rack in a predetermined set position by engaging with each other when the rack is mounted in the rack set unit.

\* \* \* \* \*